United States Patent [19]

Schirmann et al.

[11] 4,093,656

[45] June 6, 1978

[54] PROCESS FOR MAKING AZINES

[75] Inventors: Jean Pierre Schirmann, Oullins; Jean Combroux, Mornant; Serge Yvon Delavarenne, Francheville-le-Haut, all of France

[73] Assignee: Produits Chimiques Ugine Kuhlmann, Paris, France

[21] Appl. No.: 722,232

[22] Filed: Sep. 10, 1976

[30] Foreign Application Priority Data

Sep. 17, 1975 France .................... 75 28457

[51] Int. Cl.$^2$ .......................................... C07C 119/00
[52] U.S. Cl. ..................................... 260/566 B
[58] Field of Search .................. 260/566 B, 240 G

[56] References Cited

U.S. PATENT DOCUMENTS 3,943,152  3/1976  Tellier et al. ............... 260/566 B

*Primary Examiner*—Gerald A. Schwartz

*Attorney, Agent, or Firm*—Beveridge, Degrandi, Kline & Lunsford

[57] ABSTRACT

A process is described for the production of azines by contacting in the liquid phase ammonia, hydrogen peroxide and a carbonyl compound, either an aldehyde or a ketone. The reaction takes place in the presence of an amide (I) of a monocarboxylic or dicarboxylic acid, wherein at least one of the ionization constants is below $5 \times 10^{-5}$, and further in the presence of an inorganic or organic catalyst (II), having the atomic structure H—X—Y=Z, H representing hydrogen, X and Z representing oxygen or nitrogen and Y representing carbon, nitrogen, phosphorus, arsenic, antimony, sulphur, selenium or tellurium. It is possible for X, Y or Z to carry other substituents, providing valency rules are obeyed. The process is carried out in the presence of the ammonium salt (III) of the carboxylic acid corresponding to the amide (I), at the rate of at least 0.1 mole of the ammonium salt (III) per mole of hydrogen peroxide employed.

42 Claims, No Drawings

PROCESS FOR MAKING AZINES

The present invention relates to an improved process for the synthesis of azines, corresponding to the general formula:

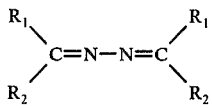

It has previously been disclosed in U.S. Pat. No. 3,972,878 issued Aug. 3, 1976 that azines may be synthesized in a process in which ammonia or, possibly, ammonia and an amine are reacted with hydrogen peroxide and a carbonyl compound of the formula

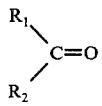

in the presence of the amide of a monocarboxylic acid, the ionization constant of which acid is below $5 \times 10^{-5}$, or of a polycarboxylic acid, at least one of the carboxylic groups of which has an ionization constant below $5 \times 10^{-5}$, and of a catalyst. This reaction may be represented by the equation:

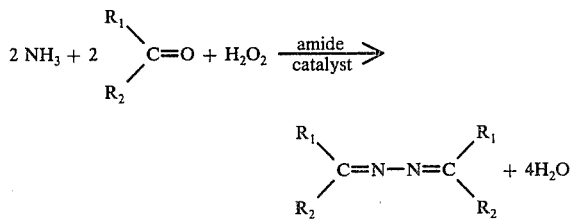

According to this process, azines may be obtained with a yield exceeding 45% by weight, relative to the hydrogen peroxide employed in the reaction, but it is not possible to exceed a yield of 78% by weight, however high the proportions of amide used.

It has now been found according to the present invention, that the yield of azines may be improved considerably; e.g., exceeding a yield of 80% and even reaching or exceeding 85% by weight. The improvement in yields is obtained when the process is carried out in the presence of the ammonium salt of the carboxylic acid as defined above. In practice, the ammonium salt is used at the rate of at least 0.1 mole per mole of the hydrogen peroxide introduced.

This result is even surprising as the reaction fails completely, if an attempt is made to produce the azines in the presence of the said ammonium salt, but in the absence of the amide.

The improvement in the yield is believed to be due to a higher selectivity of the oxidation of ammonia to azine, concomitant with a noticeable reduction in the extent of the side reactions, such as the decomposition of hydrogen peroxide.

The invention thus relates to a process for the production of azines which comprises reacting in the liquid phase: hydrogen peroxide, ammonia and a carbonyl compound, which is an aldehyde or a ketone, in the presence of the amide of a monocarboxylic or a polycarboxylic acid such as defined above, the ammonium salt corresponding to this acid and an inorganic or organic catalyst having the sequence of atoms H—X—Y—Z in a general formula:

where H is a hydrogen atom, X and Z are oxygen and nitrogen atoms and Y is either a carbon atom or a nitrogen atom or an atom of phosphorus, arsenic, antimony, sulphur, selenium or tellurium, the polyvalent atoms possibly carrying other substituents, providing that the valency rules are obeyed.

The carbonyl compound employed within the framework of the novel process has the formula:

where $R_1$ and $R_2$, which may be identical or different, represent hydrogen, a linear alkyl radical, having from 1 to 12 carbon atoms, a branched alkyl radical or cycloalkyl radical, having from 3 to 12 carbon atoms, an aromatic hydrocarbon radical having from 6 to 12 carbon atoms, or represent together a linear or branched alkylene radical having from 3 to 12 carbon atoms, these radicals being non-substituted or substituted by a chlorine, bromine or fluorine atom, by a nitro, hydroxy or alkoxy group or by an ethylenic or carboxylic ester residue and, preferably, chlorine, nitro or methoxy.

Examples of carbonyl compounds suitable for the new process are the following:

aldehydes: formaldehyde, acetaldehyde, butyraldehyde, isobutyraldehyde, n-pentanal, pivalaldehyde, benzaldehyde, the monochlorobenzaldehydes, p-nitrobenzaldehyde, anisaldehyde, β-chloropropionaldehyde, β-methoxypropionaldehyde, and the like.

ketones: acetone, 2-butanone, 2-pentanone, 3-pentanone, methyl isopropyl ketone, methyl isobutyl ketone, methyl cyclohexyl ketone, acetophenone, benzophenone, cyclobutanone, cyclopentanone, cyclohexanone, 2-methyl cyclohexanone, 3-methyl cyclohexanone, 4-methyl cyclohexanone, 2,4-dimethyl cyclohexanone, 3,3,5-trimethyl cyclohexanone, isophorone, cycloheptanone, cyclooctanone, cyclodecanone, cyclododecanone, and the like.

The preferred carbonyl compounds, however, are the lower ketones, in which $R_1$ and $R_2$, which may be identical or different, are either a linear or a branched alkyl radical having from 1 to 5 carbon atoms, and more particularly, acetone, methylethyl ketone and methylisobutyl ketone.

According to the invention, the amide is the amide of a monocarboxylic acid of formula $R_3COOH$, the dissociation constant of which is below $5 \times 10^{-5}$ and in which $R_3$ is a linear alkyl radical having from 1 to 20 carbon atoms, a branched alkyl radical or a cycloalkyl radical having from 3 to 12 carbon atoms, or a substituted phenyl radical or the amide of a polycarboxylic acid of formula $R_4(COOH)_n$, in which $R_4$ represents a linear or branched alkylidene radical having from 1 to 10 carbon atoms, and $n$ equals 1 to 2.

Examples of amides that can be used within the scope of the invention are those corresponding to formic, carbamic, acetic, propionic, n-butyric, isobutyric, pentanoic, hexanoic, octanoic, nonanoic acids, adipic and sebacic acids and substituted benzoic acids, such as o, m and p-amino-benzoic, 3,5-dihydroxybenzoic, p-hydroxy-benzoic and anisic acids. Urea and, especially, acetamide are the preferred amides.

In practice, the reactants and catalysts, employed in the process in this invention are common and easily available materials which in addition constitutes a further advantage of the invention.

The catalyst $H - X - Y = Z$, may be a phosphate, phosphite, phosphonate, polyphosphate, pyrophosphate, arsenate, bicarbonate, antimonate, stannate or a sulphonate of ammonium or of the alkali metals. In addition, the corresponding esters can be taken, particularly those of saturated aliphatic alcohols having from 1 to 5 carbon atoms. Alkali metal phosphates, and particularly disodium orthophosphate are preferred catalysts.

According to the invention, the reactants can be employed in stoichiometric quantities. However, in accordance with an advantageous embodiment of the invention, there are employed in the reaction of 0.2 to 5 moles, preferably, from 2 to 4 moles of carbonyl compound, aldehyde or ketone; 0.1 mole to 10 moles, and preferably from 2 to 4 moles of ammonia; 1 to 5 moles of amide and of ammonium salt per mole of hydrogen peroxide. The catalyst is advantageously employed at a concentration of 0.01 to 10% and, preferably, of 0.1 to 1% by weight of the reaction mixture.

According to a further detailed description of the invention, it is particularly useful to employ from 0.2 to 0.8 mole of the ammonium salt of the said carboxylic acid per mole of amide introduced. The process may be carried out in the presence of one or more hydrogen peroxide stabilizers, in particular, ethylene diamine tetracetic acid or nitrilo-triacetic acid or their sodium or ammonium salts, at a concentration of 0.01 to 1% by weight of the reaction mixture.

The new process is generally carried out in the presence of water, but it can also be conducted in the presence of an organic solvent or mixture of solvents, in order to maintain a homogeneous medium and/or ensure, at least, partial solubilization of the reactants. The preferred solvents are saturated aliphatic alcohols, having from 1 to 6 and, more particularly, from 1 to 2 carbon atoms. The alcohols used may be anhydrous or diluted with water.

Alcohols that may be used in the process are; for example, methanol, ethanol, n-propanol, isopropanol, n-butanol, sec. butanol, isobutanol, tert. butanol, the amyl alcohols, cyclohexanol, and the like. These solvents used in the process are inert with respect to the reactants and do not interfere with the reaction.

The process can be carried out over a wide temperature range, extending from 0° to 100° C, but it is preferably carried out between 30° C and 70° C. It is usually conducted at atmospheric pressure, but the new process may also be carried out at elevated pressure ranging up to 10 atmospheres, if this proves necessary in order to keep the reactants in the liquid phase.

For carrying out the process according to the invention, the reactants are brought into contact in the liquid phase and different orders of introducing them into the reactor can be employed. Thus, it is possible, for example, to introduce the reactants separately or simultaneously into a continuous or batch reactor or to introduce the hydrogen peroxide into a mixture, containing ammonia, the carbonyl compound, the amide, the ammonium salt and the catalyst, or to add ammonia or an ammoniacal solution to a mixture, containing the hydrogen peroxide, the carbonyl compound, the amide, the ammonium salt and the catalyst. It is also possible to introduce the amide and the ammonium salt into a mixture containing ammonia, hydrogen peroxide, the carbonyl compound and the catalyst, or again, to add simultaneously the ammonia or an ammoniacal solution and the hydrogen peroxide to a mixture of the carbonyl derivative, the amide, the ammonium salt and the catalyst. Which ever sequence is chosen, the reaction may be carried out in the presence or absence of a solvent, but preferably, in the presence of a hydrogen peroxide stabilizer.

Continuous operation is preferred, although the discontinuous method is equally possible.

The reactants may be used in their customary commercial form. In particular, hydrogen peroxide can be used in the form of aqueous solution of 30 to 90% by weight of $H_2O_2$ and ammonia can be used as the anhydrous material or in the form of a normal aqueous solution.

After the reaction, the azines may be separated from the reaction mixture by known methods such as liquid-liquid extraction, or fractional distillation or a combination of the two.

The products produced by the method of this invention are azines which are well known, particularly as valuable synthesil intermediates.

For example, they can be hydrolyzed, according to known methods, in order to produce hydrazine with liberation of the carbonyl compound which can be recycled. Uses for azines are described in the prior art.

The following examples illustrate the present invention. All parts and the percentages are expressed by weight.

EXAMPLE 1

The following reactants are continuously fed per hour into a reactor equipped with a mechanical stirrer, a reflux condenser and means of heating: 68.44 g of acetamide (1.16 moles); 50.4 g of 2-butanone or methyl-ethyl ketone (0.7 mole); 35.73 g of ammonium acetate (0.464 mole); 0.177 g of the disodium salt of ethylene diamine tetracetic acid (EDTA); 54.6 g of water (3.03 moles); 0.033 g of disodium phosphate and 17.18 g of an aqueous solution, 69.27% by weight of hydrogen peroxide (0.35 mole).

The reactants are maintained at a temperature of 50° C at atmospheric pressure and a current of ammonia gas is passed into the reaction mixture at a rate of about 1.2 moles per hour. When stationary state conditions have been established in the reactor, the rate of production of 2-butanone azine or methyl-ethyl ketone azine is determined by a chemical method and by gas phase chromatography. 41.65 g of 2-butanone azine (0.297 mole) are produced which corresponds to a yield of 85% with respect to the hydrogen peroxide employed.

EXAMPLE 2

A method similar to that described in example 1 is followed. 61.95 g of acetamide (1.05 moles) and 48.51 g of ammonium acetate (0.63 mole) are continuously introduced into the reactor per hour, the other reactants being fed in under the same conditions as before. Stationary state conditions having been established in the reactor, the methylethyl ketone azine formed is determined by a chemical method and by gas phase chromatography. 42.49 g (0.303 mole) of methylethyl ketone azine are formed per hour, i.e., a yield of 86.74% with respect to the hydrogen peroxide employed.

EXAMPLE 3

This is a comparative example not in accordance with the invention, but in accordance with a previously described procedure.

59 g of acetamide (1 mole); 43.2 g of 2-butanone (0.6 mole); 3 g of disodium salt of ethylene diamine tetracetic acid (EDTA); 48.5 g of water and 0.119 g of disodium phosphate are placed in a reactor. 10.6 g of ammonia (0.625 mole) are dissolved in this mixture which is subsequently heated to a temperature of 50° C and 15 g of a 68% aqueous solution of hydrogen peroxide (0.3 mole) are added during 30 minutes. The temperature is maintained at 50° C for 8 hours, in which time a current of ammonia gas is passed into the mixture at the rate of about 0.3 mole per hour. At the end of this period, 32.8 g (0.234 mole) of methylethyl ketone azine are found in the reaction mixture, which corresponds to a yield of 78%, with respect to the hydrogen peroxide.

EXAMPLE 4

This is a comparative example not in accordance with the invention.

87 g of ammonium acetate (1.13 moles); 40.93 g of 2-butanone (0.568 mole); 2 g of disodium salt of ethylene diamine tetracetic acid (EDTA); 43.44 g of water and 0.28 g of disodium phosphate are introduced into a reactor. 19.21 g of ammonia (1.13 moles) are dissolved in this mixture which is subsequently heated to a temperature of 50° C and 14.03 g of a 68.86 aqueous solution of hydrogen peroxide (0.284 mole) are introduced during 30 minutes. The temperature is maintained at 50° C for 4 hours in which time a current of ammonia gas is passed into the reaction mixture at the rate of about 0.35 mole per hour. At the end of this period, the methylethyl ketone azine is determined. It is found that no azine has been formed but that on the other hand, decomposition of hydrogen peroxide has taken place as evidenced by the considerable liberation of oxygen gas, the volume of which corresponds to the decomposition of 0.106 mole of hydrogen peroxide i.e. 37% of the quantity employed.

EXAMPLE 5

This is a comparative example but not in accordance with the invention.

59 g of acetamide (1 mole); 37.5 g of acetic acid (0.62 mole); 43.2 g of 2-butanone (0.6 mole); 3 g of disodium salt of ethylene diamine tetracetic acid (EDTA) as well as 45.8 g of aqueous solution of ammonia, 23% by weight (0.62 mole) are placed in a 300 ml reactor, equipped with a reflux condenser, a mechanical stirrer and a means of heating. A current of ammonia gas is then bubbled through the mixture during which time it is heated to 50° C.

14.8 g of a 68.6% aqueous solution of hydrogen peroxide, (0.3 mole) are then added during 30 minutes. The reaction is allowed to proceed for 8 hours at 50° C, a slow flow of ammonia being maintained. Methylethyl ketone azine formed is determined and found to be 0.121 mole which corresponds to a yield of 40.2% with respect to the hydrogen peroxide.

These comparative examples show that higher yields are obtained by utilizing the method of the present invention.

We claim:

1. In the process for the production of azines of the general formula:

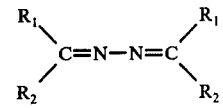

where $R_1$ and $R_2$ which may be identical or different represent hydrogen, linear alkyl groups having from 1 to 12 carbon atoms, branched alkyl or cycloalkyl groups having from 3 to 12 carbon atoms, or hydrocarbon having from 6 to 12 carbon atoms containing an aromatic ring or together $R_1$ and $R_2$ represent linear or branched alkylene having from 3 to 11 carbon atoms, these radicals being non-substituted or substituted by at least 1 chlorine, bromine or fluorine atom or by a nitro, hydroxy or alkoxy, which process comprises reacting hydrogen peroxide in the liquid phase with ammonia in the presence of a carbonyl compound, aldehyde or ketone, of general formula:

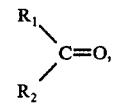

with $R_1$ and $R_2$ being defined as above, an amide of a monocarboxylic acid, the ionization constant of which is below $5 \times 10^{-5}$ or an amide of a dicarboxylic acid at least one of the acid groups of which has an ionization constant below $5 \times 10^{-5}$, and a catalyst selected from the phosphates, phosphites, phosphonates, polyphosphates, pyrophosphates, arsenates, bicarbonates, antimonates, stannates or sulphonates of ammonium or alkali metals or the saturated alkyl ($C_1$-$C_5$) esters thereof, the improvement comprising carrying out the process in the presence of the ammonium salt of the said monocarboxylic or dicarboxylic acid.

2. A process as defined in claim 1 wherein the said ammonium salt is employed at the rate of 0.1 to 10 moles per mole of hydrogen peroxide introduced.

3. A process as defined in claim 1 wherein said ammonium salt is employed at the rate of 1 to 5 moles per mole of hydrogen peroxide introduced.

4. A process according to claim 1 wherein the carbonyl compound

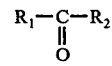

is a ketone in which $R_1$ and $R_2$ are both a linear alkyl group having from 1 to 3 carbon atoms.

5. A process as defined in claim 4 wherein the ketone is acetone or methylethyl ketone.

6. A process according to claim 1 wherein the amide is the amide of a monocarboxylic acid of formula $R_3$—COOH, in which $R_3$ is a linear alkyl having from 1 to 20 carbon atoms, branched alkyl or cycloalkyl having from 3 to 12 carbon atoms or substituted phenyl.

7. A process of claim 6 wherein the amide is of a monocarboxylic acid having from 2 to 3 carbon atoms.

8. A process according to claim 1 wherein the amide is acetamide and that the ammonium salt is ammonium acetate.

9. A process as defined in claim 1 wherein the catalyst is an alkali metal phosphate.

10. A process as defined in claim 9 wherein the catalyst is disodium orthophosphate.

11. A process according to claim 1 wherein the said amide is employed at the rate of 0.1 to 10 moles per mole of hydrogen peroxide used.

12. A process as defined in claim 11 wherein the amide is used at the rate of 1 to 5 moles per mole of hydrogen peroxide used.

13. A process according to claim 1 wherein 0.2 to 5 moles of aldehyde or ketone and of ammonia are employed in the reaction per mole of hydrogen peroxide used.

14. A process of claim 13 wherein 2 to 4 moles of aldehyde or ketone and ammonia are employed per mole of hydrogen peroxide.

15. A process according to claim 1 wherein the catalyst is employed at the rate of 0.01 to 10% by weight of the reaction mixture.

16. A process of claim 15 wherein the catalyst is employed at the rate of 0.1 to 1%.

17. A process according to claim 1 wherein the process is carried out in the presence of one or more hydrogen peroxide stabilizers at the rate of 0.01 to 1% by weight of the reaction mixture.

18. A process of claim 17 wherein the stabilizer is ethylene diamine tetracetic acid, nitrilo-tetracetic acid or their sodium or ammonium salts.

19. A process according to claim 1 wherein the process is carried out in the presence of water or of a saturated aliphatic alcohol, having from 1 to 6 carbon atoms or of an aqueous solution of the said alcohol.

20. A process according to claim 1 wherein the process is carried out at a temperature of from 0° to 100° C and at a pressure ranging from atmospheres up to 10 bar.

21. A process of claim 21 wherein the temperature ranges from 30° C. to 70° C.

22. In the process for preparing an azine or a mixture of azines which comprises reacting in the liquid phase (a) hydrogen peroxide; (b) ammonia; (c) a carbonyl compound selected from formaldehyde, acetaldehyde, butyraldehyde, isobutyraldehyde, n-pentanal, pivalaldehyde, benzaldehyde, the monochlorobenzaldehydes, p-nitrobenzaldehyde, anisaldehyde, β-chloropropionaldehyde, β-methoxypropionaldehyde, acetone, 2-butanone, 2-pentanone, 3-pentanone, methyl isopropyl ketone, methyl isobutyl ketone, methyl cyclohexyl ketone, acetophenone, benzophenone, cyclobutanone, cyclopentanone, cyclohexanone, 2-methyl cyclohexanone, 3-methyl cyclohexanone, 4-methyl cyclohexanone, 2,4-dimethyl cyclohexanone, 3,3,5-trimethyl cyclohexanone, isophorone, cycloheptanone, cyclooctanone, cyclodecanone, cyclododecanone; (d) an amide of a carboxylic acid selected from formic, carbamic, acetic, propionic, n-butyric, isobutyric, pentanoic, hexanoic, octanoic, nonanoic acids, adipic and sebacic acids and o-, m-, p-amino-benzoic, 3,5-dihydroxybenzoic, p-hydroxy-benzoic and anisic acid; (e) a catalyst selected from phosphates, phosphites, phosphonates, polyphosphates, pyrophosphates, arsenates, bicarbonates, antimonates, stannates and sulphonates of ammonium or alkali metals or the ($C_1$-$C_5$) saturated alkyl esters thereof, the improvement comprising carrying out the process in the presence of the ammonium salt of said carboxylic acid.

23. A process as defined in claim 22 wherein the said ammonium salt is employed at the rate of 0.1 to 10 moles per mole of hydrogen peroxide introduced.

24. A process as defined in claim 22 wherein said ammonium salt is employed at the rate of 1 to 5 moles per mole of hydrogen peroxide introduced.

25. A process according to claim 22 wherein the carbonyl compound $$R_1 - \underset{\underset{O}{\|}}{C} - R_2$$

is a ketone in which $R_1$ and $R_2$ are both a linear alkyl group having from 1 to 3 atoms.

26. A process as defined in claim 25 wherein the ketone is acetone or methylethyl ketone.

27. A process according to claim 22 wherein the amide is the amide of a monocarboxylic acid of formula $R_3$—COOH, in which $R_3$ is a linear alkyl having from 1 to 20 carbon atoms, branched alkyl or cycloalkyl having from 3 to 12 carbon atoms or substituted phenyl.

28. A process of claim 27 wherein the amide is of a monocarboxylic acid having from 2 to 3 carbon atoms.

29. A process according to claim 22 wherein the amide is acetamide and the ammonium salt is ammonium acetate.

30. A process as defined in claim 22 wherein the catalyst is an alkali metal phosphate.

31. A process as defined in claim 30 wherein the catalyst is disodium orthophosphate.

32. A process according to claim 22 wherein the said amide is employed at the rate of 0.1 to 10 moles per mole of hydrogen peroxide used.

33. A process as defined in claim 32 where the amide is used at the rate of 1 to 5 moles per mole of hydrogen peroxide used.

34. A process according to claim 22 wherein 0.2 to 5 moles of aldehyde or ketone and of ammonia are employed in the reaction per mole of hydrogen peroxide used.

35. A process of claim 34 wherein 2 to 4 moles of aldehyde or ketone and ammonia are employed per mole of hydrogen peroxide.

36. A process according to claim 22 wherein the catalyst is employed at the rate of 0.01 to 10% by weight of the reaction mixture.

37. A process of claim 36 wherein the catalyst is employed at the rate of 0.1 to 1%.

38. A process according to claim 22 wherein the process is carried out in the presence of one or more hydrogen peroxide stabilizers at the rate of 0.01 to 1% by weight of the reaction mixture.

39. A process of claim 38 wherein the stabilizer is ethylene diamine tetracetic acid, nitrilo-tetracetic acid or their sodium or ammonium salts.

40. A process according to claim 22 wherein the process is carried out in the presence of water or of a saturated aliphatic alcohol, having from 1 to 6 carbon atoms or of an aqueous solution of the said alcohol.

41. A process according to claim 22 wherein the process is carried out at a temperature of from 0° to 100° C and at a pressure ranging from atmospheres up to 10 bar.

42. A process of claim 41 wherein the temperature ranges from 30° C to 70° C.

* * * * *